United States Patent [19]

Schmitt

[11] Patent Number: 4,627,844
[45] Date of Patent: Dec. 9, 1986

[54] TRI-LAYER TUBING
[75] Inventor: Jerry A. Schmitt, Lionville, Pa.
[73] Assignee: High Voltage Engineering Corporation, Burlington, Mass.
[21] Appl. No.: 792,904
[22] Filed: Oct. 30, 1985
[51] Int. Cl.$^4$ .................. A61M 5/325; A61M 25/001
[52] U.S. Cl. .................................... 604/264; 604/280; 138/137; 428/36
[58] Field of Search ................. 604/264, 86, 280-284, 604/266; 138/137, 140, 103; 428/36; 264/173, 209.1

[56] References Cited

U.S. PATENT DOCUMENTS

| 3,561,493 | 2/1971 | Maillard et al. | 138/137 |
| 3,618,614 | 11/1971 | Flynn | 138/137 |
| 4,035,534 | 7/1977 | Nyberg | 138/137 |
| 4,211,741 | 7/1980 | Ostoich | 138/137 |
| 4,265,276 | 5/1981 | Hatada et al. | 428/36 |
| 4,326,532 | 4/1982 | Hammar | 604/266 |
| 4,378,803 | 4/1983 | Takagi et al. | 604/280 |

FOREIGN PATENT DOCUMENTS

| 0144629 | 6/1985 | European Pat. Off. | 604/264 |
| 0139757 | 10/1981 | Japan | 604/280 |
| 0075553 | 5/1983 | Japan | 604/280 |
| 0129137 | 7/1984 | Japan | 138/140 |

Primary Examiner—C. Fred Rosenbaum
Assistant Examiner—Jerome R. Smith, Jr.
Attorney, Agent, or Firm—Henry C. Nields

[57] ABSTRACT

A coextruded tri-layered medical-surgical tubing for the administration of common medicines such as insulin and nitroglycerin solutions is disclosed. Improved flexibility and uniformity and increased peel strength are obtained by interposing a layer of an ethylene-vinyl acetate copolymer between an outer layer of polyvinyl chloride and a core layer of low-density polyethylene. The composite tubing exhibits excellent fluid flow characteristics and is readily employed in the transportation of intravenous fluids and the like without absorbtion or contamination difficulties.

5 Claims, 2 Drawing Figures

TRI-LAYER TUBING

BACKGROUND OF THE INVENTION

Plastic tubings are extensively employed in the medical field, particularly for patient analysis and treatment procedures. Various plastics and combinations thereof are used, depending upon the specific properties the intended application demands. The selection of desired plastic materials is further limited by the use of the tubing in the in vivo treatment of human patients, as the tubing may be used in the administration of intravenous fluids or itself may be introduced into the body. Thus numerous factors must be considered in ascertaining which materials to choose.

Polyvinyl chloride (PVC) is the standard material used, made with suitable plasticizers necessary to enhance flexibility and other properties. However, such plasticizers or similar additives have a tendency to migrate, causing hazardous contamination with the fluid being administered. The contamination becomes more serious where the fluid is introduced into the body, as contamination of the blood may result, Moreover, plasticized PVC tubings have been shown to absorb nitroglycerin and insulin, and are thus unsatisfactory for the administration of these medicines. Much effort has been directed towards finding an alternative that does not suffer from the limitations of the plasticized PVC tubing. Polyurethane has been used, as in U.S. Pat. No. 4,211,741 to Ostoich. Because it is a relatively soft, flexible plastic even without additives, additives are not necessary, their absence thereby minimizing migration possibilities. In addition, it exhibits good fluid flow characteristics. However, the high cost of polyurethane has limited its use to only extraordinary applications. Some grades of ethylene-vinyl acetate copolymer (EVA) are currently being used as an outer layer, together with low-density polyethylene (LDPE) as an inner layer. Although this composite exhibits excellent peel strength, it lacks flexibility, clarity, and is easily scuffed or roughened. In addition, it cannot be solvent bonded. Since the tubing is the connecting link between a reservoir of fluid (nitroglycerin, insulin, etc.) and the patient, the method of assembly is an important consideration. Where, as here, solvent bonding cannot be utilized, an expensive, less reliable mechanical means of assembly are required, whereby a PVC layer must be pressure fit over the EVA-LDPE tubing to utilize the solvent bondable characteristics of PVC. For these reasons, the EVA-LDPE product has proven to be unsatisfactory.

The ideal product would have a thick, flexible outer layer comprised of PVC and a thin layer of LDPE, thus exploiting their respective advantages through strategic placement. Under normal extrusion conditions of temperature and pressure, however, PVC and LDPE will not bond together. Consequently, undesirable layer separation occurs. A third or "tie layer" is therefore required which will bond to both the outer PVC layer and the inner LDPE layer.

It is therefore, an object of the present invention to provide a coextruded, tri-layered, solvent bondable, soft, flexible plastic tubing which can be utilized in the administration of nitroglycerin and insulin.

Other and related objects and advantages will become evident from the following specification and claims.

SUMMARY OF THE INVENTION

The present invention is particularly directed toward a coextruded, tri-layered medical tubing employed in the administration of insulin and nitroglycerin. The outer layer of the tubing is flexible PVC made with trioctyl trimellitate plasticizer (TOTM). The middle "tie layer" is comprised of EVA, and the inner layer of LDPE. The TOTM-based PVC, developed for blood contact applications, has exhibited exceptional bond strength with the EVA resin middle layer, thereby eliminating any separation problems previously encountered. This combination of materials maintains the structural integrity of the layer tubing construction even after a gas sterilization cycle, and a fortiori, where an irradiation sterilization process is used, the strength of the bonds are actually enhanced.

DETAILED DESCRIPTION OF THE PREFERRED EMBODIMENT

Figures 1, 2:
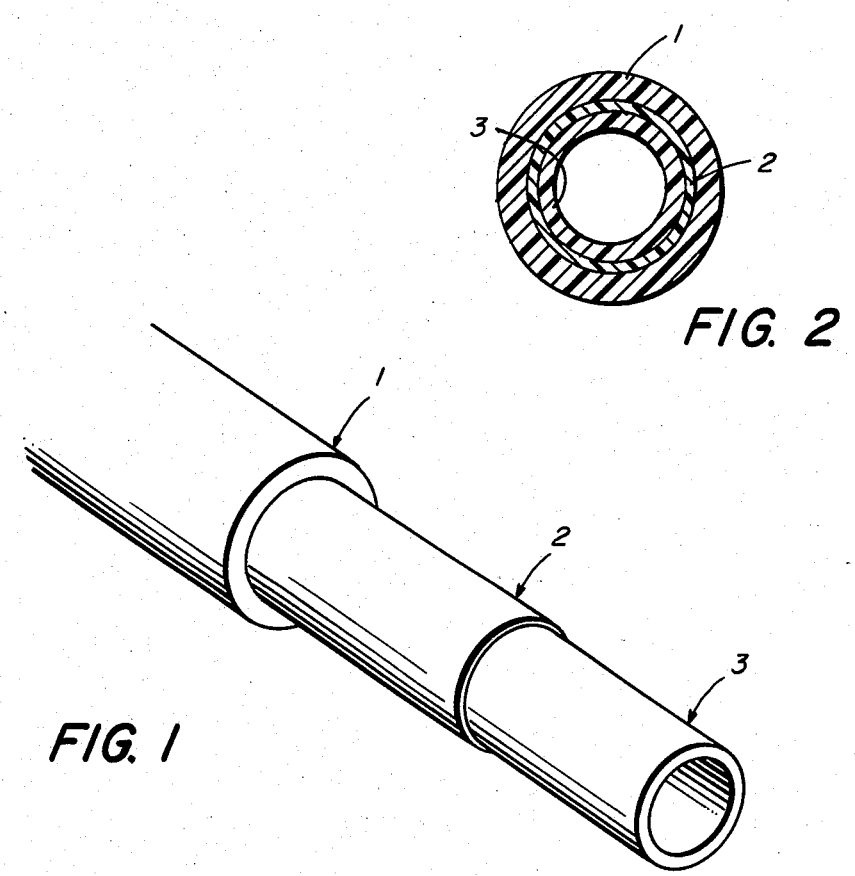

The invention can best be understood from the following detailed description of a preferred embodiment thereof, having reference to the accompanying drawing, in which:

FIG. 1 is an isometric view of a tri-layered tubing of the invention with the outer layer and middle layer broken away in order to show the construction, and FIG. 2 is an enlarged cross-section of the tri-layered tubing of the invention comprising an outer layer 1 of flexible PVC made with trioctyl trimellitate plasticizer (TOTM), a middle layer 2 of EVA, and an inner layer 3 of LDPE.

The respective thickness of each layer of tubing can be controlled by the extrusion tooling utilized, such as the "Tri Die" extrusion apparatus manufactured by the Genca Division of General Cable Company, Clearwater, Fla. Use of such sophisticated tooling results in concentric, uniform thickness, characteristics necessary for the high performance demanded by medical applications. Together with high grade plastics, the use of superior equipment will also aid in maintaining the possibility of voids, skips or cracks forming between layers, insuring that the medicines will not contact the PVC layer. General Cable's equipment is also desirable for its ease of assembly and operation, durability, flexibility, and sophisticated design to control flow. Indeed, use of such equipment allows control of each of the three layers of +0.0002 inches.

The thickness of each layer depends on the overall specifications requested by the user. To obtain the optimum balance of adhesion and clarity, an EVA layer ranging from 0.0007 to 0.0015 inches is preferred. The optimum thickness of the LDPE layer is from 0.0025 to 0.004 inches, which insures a continuous coating on the inside diameter while maintaining a balance of flexibility, adhesion and clarity in the final product. The preferred vinyl acetate content of the EVA is 28%, which allows for maximum flexibility without losing the desired extrusion characteristics.

The following example if given for illustration of the peel strength of various combinations of materials and aging conditions:

EXAMPLE I

To determine acceptable levels of adhesion of the three layers, a peel test was developed and performed on the extruded tubing. The procedure used is as follows:

1. Using a holding fixture, cut lengthwise and 8-inch length of tubing with a razor blade.
2. Using a sharp instrument such as a razor blade, scrape the inner two layers (polyolefin layer) away from the flexible PVC outer layer.
3. Peel the exposed end of the polyolefin layer away from the flexible PVC layer for a distance of 1–1.5 inches.
4. Place a small mark on the outside of the flexible PVC layer, about 2.5–3 inches from the end that the polyolefin layer has been placed.
5. Place the flexible PVC end in the upper jaws of a tensile testing machine (Instron), and place the polyolefin end in the lower jaws.
6. Start the machine. Initial jaw separation=1"; jaw separation speed=20" per minute.
7. Mark the recording chart when the peel interface reaches the mark on the outside of the flexible PVC. Record this number as the force required to separate the layer at this point.
8. Having set the machine to stop at a predetermined distance that is less than the length of the specimen, remove the specimen from the jaws after the machine has returned to the start position. Measure the peel surface length of the PVC layer and the length of the polyolefin layer and record these values.
9. Measure the width of the specimen at the previously applied mark on the flexible PVC layer. A machinist's microscope is helpful.
10. Calculate the "peel strength" of the layers by dividing the force at the mark (recorded in step 7) by the width at the mark (recorded in step 9). This value is the peel strength of the flexible PVC layer to the polyolefin layer, expressed as pounds per inch of width (P.I.W.).

The results of representative experiments using the foregoing procedure are shown in Table 1. Table 1 indicates that tri-layer tubing utilizing dioctyl phthalate (DOP) plastizer based PVC in the outer layer has a significant reduction in peel strength after oven aging for twelve hours @ 135° F.(135° F. was selected as a typical temperature for a gas sterilization cycle.) Tri-layer tubing utilizing trioctyl trimellitate (TOTM) plasticizer based PVC in the outer layer suffers no loss of peel strength under the same conditions.

Further testing of the DOP-PVC tri-layer tubing and the TOTM-PVC tri-layer tubing for sixty hours @ 140° F. resulted in the DOP-PVC tri-layer tubing losing essentially all of its peel strength. The TOTM-PVC tri-layer tubing retains a much higher percentage of its peel strength under these exceptional conditions.

TABLE 1

PEEL TEST RESULTS

| TIME @ TEMPERATURE OUTER LAYER/MIDDLE LAYER/INNER LAYER | 24 HRS. @ 78° F. PEEL STRENGTH[1] | 12 HRS. @ 135° F. PEEL STRENGTH[1] | 60 HRS. @ 140° F. PEEL STRENGTH[1] |
|---|---|---|---|
| DOP-PVC/EVA/LDPE | 3.2 | 1.9 | 0.01 |
| TOTM-PVC/EVA/LDPE | 3.6 | 3.6 | 0.79 |

[1]Units are pounds per inches of width as outlined in example 1.

Having thus described the principles of the invention, together with an illustrative embodiment thereof, it is to be understood that although specific terms are employed they are used in a generic and descriptive sense, and not for purposes of limitation, the scope of the invention being set forth in the following claims:

I claim:

1. A coextruded tri-layered medical-surgical tubing for the administration of common medicines such as insulin and nitroglycerin solutions, said tubing comprising an outer layer of polyvinyl chloride, a core layer of low-density polyethylene, and an intermediate layer of an ethylene-vinyl acetate copolymer interposed between said outer layer and said core layer.

2. A tubing in accordance with claim 1 wherein said outer layer includes trioctyl trimellitate as a plasticizer.

3. A tubing in accordance with claim 2 wherein the thickness of said intermediate layer is in the range 0.0007 to 0.0015 inches and the thickness of said core layer is in the range 0.0025 to 0.004 inches.

4. A tubing in accordance with claim 2 wherein said intermediate layer has a vinyl acetate content of 28 percent by weight of said copolymer.

5. A method of making tri-layered medical-surgical tubing for the administration of common medicines such as insulin and nitroglycerin solutions comprising simultaneously and coaxially extruding an outer layer of polyvinyl chloride containing a plasticizing amount of trioctyl trimellitate, a core layer of low-density polyethylene, and an intermediate layer of an ethylene-vinyl acetate copolymer in such a manner that upon extrusion said intermediate layer is intimately bonded to said outer layer and to said core layer.

* * * * *